(12) United States Patent
Cheikh et al.

(10) Patent No.: US 7,518,035 B2
(45) Date of Patent: Apr. 14, 2009

(54) PROMOTER MOLECULES FOR USE IN PLANTS

(75) Inventors: Nordine Cheikh, Chesterfield, MO (US); Molian Deng, Grover, MO (US); Steve He, St. Louis, MO (US); Wei Wu, St. Louis, MO (US); Xiaoyun Wu, Chesterfield, MO (US); Zhidong Xie, Maryland Heights, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/086,904

(22) Filed: Mar. 22, 2005

(65) Prior Publication Data

US 2005/0262582 A1 Nov. 24, 2005

Related U.S. Application Data

(60) Provisional application No. 60/555,632, filed on Mar. 23, 2004.

(51) Int. Cl.
*C12N 15/63* (2006.01)
*C12N 15/82* (2006.01)
*C12N 5/10* (2006.01)
*C12N 15/00* (2006.01)
*A01H 5/00* (2006.01)

(52) U.S. Cl. .............. 800/287; 800/278; 800/295; 435/320.1; 435/468; 536/24.1; 536/23.1

(58) Field of Classification Search .............. None
See application file for complete search history.

(56) References Cited

U.S. PATENT DOCUMENTS

| 5,530,196 A | 6/1996 | Fraley et al. |
| 5,641,876 A | 6/1997 | McElroy et al. |
| 6,051,753 A | 4/2000 | Comai et al. |

OTHER PUBLICATIONS

Kim et al 1994, Plant Molecular Biology 24:105-117.*
Donald et al 1990, EMBO J. 9:1717-1726.*
Dolferus et al 1994, Plant Physiology 105:1075-1087.*
Welsch et al 2003 Planta 216:523-534.*
Piechulla et al 1998 Plant Molecular Biology 38:655-662.*
Cho et al 2002 The Plant Cell 14:3237-3253.*
GenBank Accession No. AP003562, Nov. 30, 2004.
GenBank Accession No. BAB92738, Aug. 31, 2004.
Meijer et al., "Cell cycle controls and the development of plant form," Current Opinion in Plant Biology, 4(1):44-49, 2001.
NCBI Gene ID No. 4323966, *Oryza sativa* (japonica cultivar-group), Os01g0516700, Apr. 19, 2007.
NCBI Gene ID No. 4323968, *Oryza sativa* (japonica cultivar-group), Os01g0516900, Dec. 12, 2006.

(Continued)

*Primary Examiner*—Russell Kallis
*Assistant Examiner*—Brent Page
(74) *Attorney, Agent, or Firm*—Sonnenschein Nath & Rosenthal LLP (57) ABSTRACT

The present invention provides nucleic acid molecules isolated from *Zea mays* and *Oryza sativa* and useful for expressing transgenes in plants. The present invention also provides expression constructs containing the nucleic acid molecules useful for expressing transgenes in plants. The present invention also provides transgenic plants and seeds containing the nucleic acid molecules useful for expressing transgenes in plants.

22 Claims, 2 Drawing Sheets

ROOT     STEM     LEAF

SEED     SAM and Leaf Primordia     Infloresence and Floral Meristem

OTHER PUBLICATIONS

NCBI Gene ID No. 4323969, *Oryza sativa* (japonica cultivar-group), Os01g0517000, Jan. 5, 2007.

NCBI Gene ID No. 4323970, *Oryza sativa* (japonica cultivar-group), Os01g0517500, Apr. 19, 2007.

NCBI Gene ID No. 4323973, *Oryza sativa* (japonica cultivar-group), Os01g0518000, Apr. 19, 2007.

Russell et al., "Tissue-specific expression in transgenic maize of four endosperm promoters from maize and rice," Transgenic Res., 6(2):157-168, 1997.

* cited by examiner

SEQUENCE LISTING

<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 1
ttgtgttgca agcaacagtt ctag                                         24

```
<210> SEQ ID NO 2
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 2
agttctagcc atgaaggcat tgtc                                             24

<210> SEQ ID NO 3
<211> LENGTH: 38
<212> TYPE: DNA
<213> ORGANISM: Artificial sequence
<220> FEATURE:
<223> OTHER INFORMATION: Oligonucleotide primer

<400> SEQUENCE: 3
gccggatcca gatcttgtga atcagtggt ctattgtg                                38

<210> SEQ ID NO 4
<211> LENGTH: 1508
<212> TYPE: DNA
<213> ORGANISM: Zea mays
<220> FEATURE:
<221> NAME/KEY: unsure
<222> LOCATION: (1)..(1508)
<223> OTHER INFORMATION: unsure at all n locations

<400> SEQUENCE: 4
ccttgtttgg actccagaaa atttacggga gttggtggag caggtcatta agtactataa       60
aaaatcatgt agctgaagct gcaagtattt agaagacatt tagataagtt attttattta      120
ttatttagat taaaaaaatt taaaactatt taaattgata ttataaacta cagctccaca      180
ctggagctag atcctggagt cattacaaac acccccttaa tgggaaaaga gaagataatg      240
tatatctaat tattgtttct gtgtcaccta tagctattag ttcaaaactt cataatcact      300
ggtacaaata agctctagag aggcggttcg gaacccattt ttattgttgt ttttcaaaac      360
cactagtgtt agggaccgcc agtggaaact gaaacgccat tggaaattga ttttcactga      420
tggtgagcta agaaaaccgc cattggtaat cctttgcaga aaacataaac taggttttaa      480
aaatagtaaa caaatatttt tattaggaga ggccccacct agtcgcacca ttttcacgc       540 attattcacg cgctacgcaa ccaatggtaa ttgaacctca gagacttcac tcttgtgtag      600
cctcctttgc cactccacta aacacttact tgntgtcttg attgcatttt gttgcccaca      660
tattagaaca aaccagagtg taaattgatt gtttgaggcc tgtaaccaaa ttccaaatga      720 aaagtagtc aactactaaa ttgataatt gtttatgttc taccactttt attttggtac        780
ttttcccatc gnaggcggtt tgtaaaattt gcattttaag ttttacaaat ttcaatgaaa      840
ttttgagagc ccaaatgatt tcaaataaaa agttgtcaa ctacaatgtt ttataacttt       900
taatttggtg gttttaaaac aagctcattt gaaaaactaa aaagatcgat tctacatgat      960
ttttaggtcg attttttaag gaatcgcctg tacaaatatt tctactgaca gttttttaaga   1020 aaccacctgt ggaaatcata gatttgtact agcggttttt ctcaagtaac tgctagtaga   1080
aatatggtgg ttttcttaag aaaactgttt gtaggaatgc acgatttata taaatggatt   1140
tgttaagaaa accgctagtg gaatgttctt tcaactaacg gttattgagt cgtgacagcc   1200
aatttaattt ccttgataac taaaagcggc tgtaaaaatt agaccatgat gtaggcacgg   1260
agctgttttg tactgaatgc gcccactgtt ttgttggaaa agtgcatgta cttattattc   1320
```

```
attctgttta tttctagctg gcattcagtt cttacagcca cagattatgc aaaacgccta    1380
tttctgccag caaatttaca ggaaaagtca tggactttc cgggttattt tcctataagt    1440
acagccattc ctttcactta caggccccaa cattagcaca aagaacacaa tagaccactg    1500
atttaaca                                                            1508
```

<210> SEQ ID NO 5
<211> LENGTH: 1310
<212> TYPE: DNA
<213> ORGANISM: Zea mays
<220> FEATURE:
<221> NAME/KEY: unsure
<222> LOCATION: (1)..(1310)
<223> OTHER INFORMATION: unsure at all n locations

<400> SEQUENCE: 5

```
gggatccact agttctagag cggccgcgtt aacaagcttg gtcgacggcc cgggctggtc     60
cttgtttgga ctccagaaaa tttacgggag ttggtggagc aggtcattaa gtactataaa    120
aaatcatgta gctgaagctg caagtattta aagacatttt agataagtta ttttatttat    180
tatttagatt aaaaaaattt aaaactattt aaattgatat tataaactac agctccacac    240
tggagctaga tcctggagtc attacaaaca ccccttaat gggaaaagag aagataatgt     300
atatctaatt attgtttctg tgtcacctat agctattagt tcaaaacttc ataatcactg    360
gtacaaataa gctctagaga ggcggttcgg aacccatttt tattgttgtt tttcaaaacc    420
actagtgtta gggaccgcca gtggaaactg aaacgccatt ggaaattgat tttcactgat    480
ggtgagctaa gaaaaccgcc attggtaatc ctttgcagaa aacataaact aggttttaaa    540
aatagtaaac aaatatttttt attaggagag gccccaccta gtcgcaccat ttttcacgca    600
ttattcacgc gctacgcaac caatggtaat tgaacctcag agacttcact cttgtgtagc    660
ctcctttgcc actccactaa acacttactt gntgtcttga ttgcattttg ttgcccacat    720
attagaacaa accagagtgt aaattgattg tttgaggcct gtaaccaatt aggtcgattt    780
tttaaggaat cgcctgtaca aatatttcta ctgacagttt ttaagaaacc acctgtggaa    840
atcatagatt tgtactagcg gttttttctca agtaactgct agtagaaata tggtggtttt    900
cttaagaaaa ctgtttgtag gaatgcacga tttatataaa tggatttgtt aagaaaaccg    960
ctagtggaat gttcttttcaa ctaacggtta ttgagtcgtg acagccaatt taatttcctt   1020
gataactaaa agcggctgta aaaattagac catgatgtag gcacggagct gttttgtact   1080
gaatgcgccc actgttttgt tggaaaagtg catgtactta ttattcattc tgtttatttc   1140
tagctggcat tcagttctta cagccacaga ttatgcaaaa cgcctatttc tgccagcaaa   1200
tttacaggaa aagtcatgga ctttttccggg ttattttcct ataagtacag ccattccttt   1260
cacttacagg ccccaacatt agcacaaaga acacaataga ccactgattt                1310
```

<210> SEQ ID NO 6
<211> LENGTH: 542
<212> TYPE: DNA
<213> ORGANISM: Zea mays

<400> SEQUENCE: 6

```
ttaggtcgat tttttaagga atcgcctgta caaatatttc tactgacagt ttttaagaaa     60
ccacctgtgg aaatcataga tttgtactag cggttttttct caagtaactg ctagtagaaa   120
tatggtggtt ttcttaagaa aactgtttgt aggaatgcac gatttatata atggatttg    180 ttaagaaaac cgctagtgga atgttctttc aactaacggt tattgagtcg tgacagccaa   240
```

```
tttaatttcc ttgataacta aaagcggctg taaaaattag accatgatgt aggcacggag    300
ctgttttgta ctgaatgcgc ccactgtttt gttggaaaag tgcatgtact tattattcat    360
tctgttattt tctagctggc attcagttct tacagccaca gattatgcaa aacgcctatt    420
tctgccagca aatttacagg aaaagtcatg acttttccg ggttattttc ctataagtac    480
agccattcct ttcacttaca ggccccaaca ttagcacaaa gaacacaata gaccactgat    540
tt                                                                   542
```

<210> SEQ ID NO 7
<211> LENGTH: 1804
<212> TYPE: DNA
<213> ORGANISM: Oryza sativa

<400> SEQUENCE: 7

```
cttcatctct aacaataaat acttcttaac ctatcctccc agtaaataaa atatattggg     60
gaaagtatta ctccaatggc caattcagca cagtgaatct ctgttttggt ttggcgcaaa    120
aaaagtatat gatgccacac accttccaaa tttaaatatc atacctttga attacccaaa    180
attgtactga actacacttg aaattaaaaa aaatctaatt ctgcaaactt tataatttaa    240
gtaacttaaa catttttttt atcgtaagtg ttagacacat cttccaaatt tagcttgaca    300
tataaattaa ttctattaga atcatccact agaggatgat ggactggagt ccaacacact    360
acaccttagc gccaccacgc acgttaaaaa ggtcaaaaag ccaacggtct aactctaaat    420
ttacgtcatt ccaaaaaaaa caaatgtata ttaaacactaa ttgcaaaatg atataacata    480
tattaatttt ccgttttaac tggatagtca agataaactt attaacatac atttcacatg    540
tagatgtata tggacgggct atatggccag aacgccaaca gaatataagg gggcgtgaag    600
ggagctatgc agtggtgagt acgatgggaa ggtagcagcg acgatgagcg tgtgttagga    660
ggggtacgag tatgagtaat gatgtgtgag ttttgaaaaa aaaatagtga tatgtgtgtc    720
tgcgttttc atttacgtaa ttgtaataaa aaaaatatgt gtgtattctc acatgttaat     780
ttcactctac caatgacttt tgactttca ttaaccgtaa ttcgtcattt acattgtgat     840
cacaaatttc agctaattac tatcaacaac acgtaaacac atttaaaaag agatgttata    900
gtcacgtgga tgcacaatat aatgtgctag taattatgaa agtacttccc tcaaggcacc    960
caatgccact gtaaaaatta gatgataagt gatcccagca agcgttgtga gtggtacggt   1020
gaacataaat tactggtcat atgcagggaa gcataacgtt gttgtagtta gctagcttct   1080
catgccatca ttttttctcac ttcaaaatat atttttttca tgaacaattt atcccaatta   1140
tgatctgatt ataccattgt tttcgttgca actaaatctt gataacaaga tctcagttgg   1200
ttatattcaa gtgaaagaaa atatgtgtac caaccattaa aatttaatat ttcatacatg   1260
agaagtcaat gtttcaattc gaatttgacc atattgcata tttaaagttt ttgtgttgca   1320
ttggattttt tctaaatgtc acatatagtg tcgttcgaat gttacaacaa gtacttttgc   1380
aaattgttgt tacaaaagtt tgcttgtttt cgtgatactt actacactta aataagaacg   1440
caacatccat aaaaggtagt gttgtagatc aatgatgttg catgcaactc acgcgacaca   1500
tggtattgat ggcataaggc atgccaagca tgacctatca tcgcccaagc actataaacc   1560
aaaaatttgc agtttctttt gttcaaatgg acaatgccaa ctatgtgctt gctctagctt   1620
tttcaagtac aagaaaatat gtggtcccac acttttctgg cccatagatt atgcaaagca   1680
tcttttggcg ccagtggatt ttcttaataa aacaagtatt gctcattgat ttattgctat   1740
```

| aaatgcaccc catcctttca cttactaacc agataggcct aagaatcctc ttgtgttcac | 1800 |
| catg | 1804 |

<210> SEQ ID NO 8
<211> LENGTH: 1677
<212> TYPE: DNA
<213> ORGANISM: Oryza sativa

<400> SEQUENCE: 8

| cttcatctct aacaataaat acttcttaac ctatcctccc agtaaataaa atatattggg | 60 |
| gaaagtatta ctccaatggc caattcagca cagtgaatct ctgttttggt ttggcgcaaa | 120 |
| aaaagtatat gatgccacac accttccaaa tttaaatatc ataccttttga attacccaaa | 180 |
| attgtactga actacacttg aaattaaaaa aaatctaatt ctgcaaactt tataatttaa | 240 |
| gtaacttaaa catttttttt atcgtaagtg ttagacacat cttccaaatt tagcttgaca | 300 |
| tataaattaa ttctattaga atcatccact agaggatgat ggactggagt ccaacacact | 360 |
| acaccttagc gccaccacgc acgttaaaaa ggtcaaaaag ccaacggtct aactctaaat | 420 |
| ttacgtcatt ccaaaaaaaa caatgtgtata ttaacactaa ttgcaaaatg atataacata | 480 |
| tattaatttt ccgttttaac tggatagtca agataaactt attaacatac atttcacatg | 540 |
| tagatgtata tggacgggct atatggccag aacgccaaca gaatataagg gggcgtgaag | 600 |
| ggagctatgc agtggtgagt acgatgggaa ggtagcagcg acgatgagcg tgtgttagga | 660 |
| ggggtacgag tatgagtaat gatgtgtgag ttttgaaaaa aaaatagtga tatgtgtgtc | 720 |
| tgcgttttc atttacgtaa ttgtaataaa aaaaatatgt gtgtattctc acatgttaat | 780 |
| ttcactctac caatgacttt ttgactttca ttaaccgtaa ttcgtcattt acattgtgat | 840 |
| cacaaatttc agctaattac tatcaacaac acgtaaacac atttaaaaag atgttata | 900 |
| gtcacgtgga tgcacaatat aatgtgctag taattatgaa agtacttccc tcaaggcacc | 960 |
| caatgccact gtaaaaatta gatgataagt gatcccagca agcgttgtga gtggtacggt | 1020 |
| gaacataaat tactggtcat atgcagggaa gcataacgtt gttgtagtta gctagcttct | 1080 |
| catgccatca ttttctcat gtgtaccaac cattaaaatt taatatttca tacatgagaa | 1140 |
| gtcaatgttt caattcgaat ttgaccatat tgcatattta aagttttgt gttgcattgg | 1200 |
| atttttcta aatgtcacat atagtgtcgt tcgaatgtta caacaagtac ttttgcaaat | 1260 |
| tgttgttaca aaagttttgct tgttttcgtg atacttacta cacttaaata agaacgcaac | 1320 |
| atccataaaa ggtagtgttg tagatcaatg atgttgcatg caactcacgc gacacatggt | 1380 |
| attgatggca taaggcatgc caagcatgac ctatcatcgc ccaagcacta taaaccaaaa | 1440 |
| atttgcagtt tcttttgttc aaatggacaa tgccaactat gtgcttgctc tagctttttc | 1500 |
| aagtacaaga aaatatgtgg tcccacactt ttctggccca tagattatgc aaagcatctt | 1560 |
| ttggcgccag tggattttct taataaaaca agtattgctc attgatttat tgctataaat | 1620 |
| gcaccccatc ctttcactta ctaaccagat aggcctaaga atcctcttgt gttcacc | 1677 |

<210> SEQ ID NO 9
<211> LENGTH: 579
<212> TYPE: DNA
<213> ORGANISM: Oryza sativa

<400> SEQUENCE: 9

| atgtgtacca accattaaaa tttaatattt catacatgag aagtcaatgt ttcaattcga | 60 |
| atttgaccat attgcatatt taaagttttt gtgttgcatt ggattttttc taaatgtcac | 120 |

-continued

```
atatagtgtc gttcgaatgt tacaacaagt acttttgcaa attgttgtta caaaagtttg      180
cttgttttcg tgatacttac tacacttaaa taagaacgca acatccataa aaggtagtgt      240
tgtagatcaa tgatgttgca tgcaactcac gcgacacatg gtattgatgg cataaggcat      300
gccaagcatg acctatcatc gcccaagcac tataaaccaa aaatttgcag tttcttttgt      360
tcaaatggac aatgccaact atgtgcttgc tctagctttt tcaagtacaa gaaaatatgt      420
ggtcccacac ttttctggcc catagattat gcaaagcatc ttttggcgcc agtggatttt      480
cttaataaaa caagtattgc tcattgattt attgctataa atgcacccca tcctttcact      540
tactaaccag ataggcctaa gaatcctctt gtgttcacc                              579
```

PROMOTER MOLECULES FOR USE IN PLANTS

This application claims the benefit of U.S. provisional patent application No. 60/555,632 filed Mar. 23, 2004, incorporated herein by reference in its entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01124.rpt, which is 12,288 bytes (measured in MS-DOS) and was created on Mar. 21, 2005, are hereby incorporated by reference.

FIELD OF THE INVENTION

The invention relates to the field of plant molecular biology and plant genetic engineering and nucleic acid molecules useful for the expression of transgenes in plants.

BACKGROUND

One of the goals of plant genetic engineering is to produce plants with agronomically desirable characteristics or traits. Promoters are nucleic acid molecules which comprise the 5' regulatory elements that play an integral part in the overall expression of genes in living cells. Isolated promoters that function in plants are useful for controlling the expression of operably linked transgenes and thereby modifying plant phenotypes through the methods of genetic engineering.

Many constitutive promoters are available and are useful for providing good overall expression of an operably linked transgene. Examples of such promoters are P-FMV, the promoter from the 35S transcript of the Figwort mosaic virus, (U.S. Pat. No. 6,051,753); P-CaMV 35S, the promoter from the 35S RNA transcript of the Cauliflower mosaic virus, (U.S. Pat. No. 5,530,196); P-Rice Actin 1, the promoter from the actin 1 gene of *Oryza sativa*, (U.S. Pat. No. 5,641,876); and P-NOS, the promoter from the nopaline synthase gene of *Agrobacterium tumefaciens*. These promoters provide some level of gene expression in most or all of the tissues of a plant during most or all of the plant's lifespan. Alternately, many promoters are available with more limited expression patterns and are characterized by their tissue specificity, temporal specificity, or developmental specificity. These promoters are useful for the targeted expression of an operably linked transgene in plants. Ultimately, optimal expression of a transgene for producing plants with agronomically desirable characteristics or traits may require such targeted expression. Such targeted expression often requires a promoter having a specific expression pattern which may not be readily available in known promoters.

An example of a desirable targeted expression pattern which is not readily available in known promoters is expression in the maize endosperm during the early stages of kernel development. Endosperm cell division occurs from 5 to 15 days after pollination (DAP). A promoter having an expression pattern active from 5 to 15 DAP would be useful for driving expression of a transgene for a variety of purposes such as preventing kernel abortion in response to stress; promoting cell division to increase endosperm cell number which may increase kernel size and therefore increase grain yield; and altering kernel composition to increase or decrease components such as oil, protein, or starch. The specificity of the promoter for endosperm expression is also important, as ectopic activity in non-targeted tissues has been reported to be associated with the disruption of pattern formation and organogenesis, resulting in deleterious plant growth and development (Meijer M, Murray J A. "Cell cycle controls and the development of plant form." *Current Opinion in Plant Biology* 2001 February 4(1):44-49).

Currently characterized cereal endosperm promoters are mainly those of grain storage proteins or those involved in carbohydrate metabolism both of which are turned on at relatively late stages during kernel development (Russell D A, Fromm M E. "Tissue-specific expression in transgenic maize of four endosperm promoters from maize and rice." *Transgenic Research* 1997 March 6(2):157-168). The present invention provides a novel promoter capable of driving expression of an operably linked transgene in the endosperm during the early stages of kernel development.

SUMMARY

In one embodiment the invention provides promoters isolated from *Zea mays* and *Oryza sativa* and provided as SEQ ID NO: 4-9 useful for expressing transgenes in plants. In another embodiment the invention provides constructs comprising the promoter and useful for expressing transgenes in plants. In another embodiment the invention provides a transgenic plant containing the promoter and the seed of the transgenic plant.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides promoters capable of driving the expression of an operably linked transgene. The design, construction, and use of these promoters is one object of this invention. The promoter sequences, provided as SEQ ID NO: 4-9, are capable of transcribing operably linked nucleic acid molecules in endosperm tissues during the early stages of kernel development and therefore can selectively regulate expression of transgenes in this tissue.

As used herein, the term "nucleic acid molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "nucleic acid sequence" refers to the sequence of a nucleic acid molecule. The nomenclature for DNA bases as set forth at 37 CFR §1.822 is used.

As used herein, the term "promoter" refers to a nucleic acid molecule that is involved in recognition and binding of RNA polymerase II and other proteins (trans-acting transcription factors) to initiate transcription. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

A promoter comprises subfragments that have promoter activity. Subfragments may comprise enhancer domains and may be useful for constructing chimeric promoters. Subfragments of SEQ ID NO: 4 comprise at least about 75, 85, 90, 95, 110, 125, 250, 400, 750, 1000, 1300, and 1500 contiguous nucleotides of the nucleic acid sequence of SEQ ID NO: 4, up to the full 1508 nucleotides of SEQ ID NO: 4. Subfragments of SEQ ID NO: 7 comprise at least about 95, 110, 125, 250, 400, 750, 1000, 1300, 1500, and 1800 contiguous nucleotides of the nucleic acid sequence of SEQ ID NO: 7, up to the full 1804 nucleotides of SEQ ID NO: 7.

As used herein, the term "enhancer domain" refers to a cis-acting transcriptional regulatory element, a.k.a. cis-element, which confers an aspect of the overall control of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked nucleic acid sequences are encompassed by the present invention.

As used herein, the term "chimeric" refers to the product of the fusion of portions of two or more different nucleic acid molecules. As used herein, the term "chimeric promoter" refers to a promoter produced through the manipulation of known promoters or other nucleic acid molecules. Such chimeric promoters may combine enhancer domains that can confer or modulate gene expression from one or more promoters, for example, by fusing a heterologous enhancer domain from a first promoter to a second promoter with its own partial or complete regulatory elements. Thus, the design, construction, and use of chimeric promoters according to the methods disclosed herein for modulating the expression of operably linked nucleic acid sequences are encompassed by the present invention.

As used herein, the term "percent sequence identity" refers to the percentage of identical nucleotides in a linear nucleic acid sequence of a reference nucleic acid molecule (or its complementary strand) as compared to a test nucleic acid molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more nucleic acid sequences may be to a full-length nucleic acid sequence or a portion thereof, or to a longer nucleic acid sequence.

As used herein, the term "substantial percent sequence identity" refers to a percent sequence identity of at least about 70% sequence identity, at least about 80% sequence identity, at least about 90% sequence identity, or even greater sequence identity, such as about 98% or about 99% sequence identity. Thus, one embodiment of the invention is a nucleic acid molecule that has at least about 70% sequence identity, at least about 80% sequence identity, at least about 90% sequence identity, or even greater sequence identity, such as about 98% or about 99% sequence identity with a nucleic acid sequence described herein. Nucleic acid molecules that are capable of regulating transcription of operably linked transcribable nucleic acid molecules and have a substantial percent sequence identity to the nucleic acid sequences of the promoters provided herein are encompassed within the scope of this invention.

Promoter Isolation and Modification Methods

Any number of methods well known to those skilled in the art can be used to isolate fragments of a promoter disclosed herein. For example, PCR (polymerase chain reaction) technology can be used to amplify flanking regions from a genomic library of a plant using publicly available sequence information. A number of methods are known to those of skill in the art to amplify unknown nucleic acid molecules adjacent to a core region of known nucleic acid sequence. Methods include but are not limited to inverse PCR (IPCR), vectorette PCR, Y-shaped PCR, and genome walking approaches. Nucleic acid fragments can also be obtained by other techniques such as by directly synthesizing the fragment by chemical means, as is commonly practiced by using an automated oligonucleotide synthesizer. For the present invention, the nucleic acid molecules were isolated from genomic DNA by designing PCR primers based on available sequence information.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., nucleic acid molecules, plasmids, etc.), as well as the generation of recombinant organisms and the screening and isolation of nucleic acid molecules.

Constructs

As used herein, the term "construct" refers to any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

As used herein, the term "operably linked" refers to a first nucleic acid molecule, such as a promoter, connected with a second transcribable nucleic acid molecule, such as a gene of interest, where the nucleic acid molecules are so arranged that the first nucleic acid molecule affects the function of the second nucleic acid molecule. The two nucleic acid molecules may be part of a single contiguous nucleic acid molecule and may be adjacent. For example, a promoter is operably linked to a gene of interest if the promoter regulates or mediates transcription of the gene of interest in a cell.

As used herein, the term "transcribable nucleic acid molecule" refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual*, 3$^{rd}$ edition Volumes 1, 2, and 3 (2000) J. F. Sambrook, D. W. Russell, and N. Irwin, Cold Spring Harbor Laboratory Press.

Constructs of the present invention would typically contain a promoter operably linked to a transcribable nucleic acid molecule operably linked to a 3' transcription termination nucleic acid molecule. In addition, constructs may include but are not limited to additional regulatory nucleic acid molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA nucleic acid molecule which can play an important role in translation initiation and can also be a genetic component in a plant expression construct. For example, non-translated 5' leader nucleic acid molecules derived from heat shock protein genes have been demonstrated to enhance gene expression in plants (see for example, U.S. Pat. No. 5,659,122 and U.S. Pat. No. 5,362,865, all of which are hereby incorporated by reference). These additional upstream and downstream regulatory nucleic acid molecules may be derived from a source that is native or heterologous with respect to the other elements present on the promoter construct.

Thus, one embodiment of the invention is a promoter such as provided in SEQ ID NO: 4-9, operably linked to a transcribable nucleic acid molecule so as to direct transcription of said transcribable nucleic acid molecule at a desired level or in a desired tissue or developmental pattern upon introduction of said construct into a plant cell. In some cases, the transcribable nucleic acid molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable nucleic acid molecules for incorporation into constructs of the present invention include, for example, nucleic acid molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or nucleic acid molecule that is introduced into a recipient cell. The type of nucleic acid molecule included in the exogenous nucleic acid molecule can include a nucleic acid molecule that is already present in the plant cell, a nucleic acid molecule from another plant, a nucleic acid molecule from a different organism, or a nucleic acid molecule generated externally, such as a nucleic acid molecule containing an antisense message of a gene, or a nucleic acid molecule encoding an artificial or modified version of a gene.

The promoters of the present invention can be incorporated into a construct using marker genes as described and tested in transient analyses that provide an indication of gene expression in stable plant systems. As used herein the term "marker gene" refers to any transcribable nucleic acid molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable nucleic acid molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Exemplary marker genes for transient analyses of the promoters or promoter fragments of the present invention include a GUS gene (U.S. Pat. No. 5,599,670, hereby incorporated by reference) or a GFP gene (U.S. Pat. No. 5,491,084 and U.S. Pat. No 6,146,826, both of which are hereby incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a nucleic acid molecule of the present invention as shown in SEQ ID NO: 4-9 is incorporated into a construct such that a promoter of the present invention is operably linked to a transcribable nucleic acid molecule that provides for a selectable, screenable, or scorable marker. Markers for use in the practice of the present invention include, but are not limited to transcribable nucleic acid molecules encoding β-glucuronidase (GUS), green fluorescent protein (GFP), luciferase (LUC), proteins that confer antibiotic resistance, or proteins that confer herbicide tolerance. Useful antibiotic resistance markers, including those genes encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Nucleic acid molecules encoding proteins involved in herbicide tolerance are known in the art, and include, but are not limited to a nucleic acid molecule encoding 5-enolpyruvylshikimate-3-phosphate synthase (EPSPS) described in U.S. Pat. No. 5,627,061, U.S. Pat. No 5,633,435, and U.S. Pat. No 6,040,497 and aroA described in U.S. Pat. No. 5,094,945 for glyphosate tolerance, all of which are hereby incorporated by reference; a nucleic acid molecule encoding bromoxynil nitrilase (Bxn) described in U.S. Pat. No. 4,810,648 for Bromoxynil tolerance, which is hereby incorporated by reference; a nucleic acid molecule encoding phytoene desaturase (crtI) described in Misawa et al, (1993) *Plant Journal* 4:833-840 and Misawa et al, (1994) *Plant Journal* 6:481-489 for norflurazon tolerance; a nucleic acid molecule encoding acetohydroxyacid synthase (AHAS, aka ALS) described in Sathasiivan et al. (1990) *Nucleic Acids Research* 18:2188-2193 for tolerance to sulfonylurea herbicides; and the bar gene described in DeBlock, et al. (1987) *EMBO Journal* 6:2513-2519 for glufosinate and bialaphos tolerance.

In one embodiment of the invention, a nucleic acid molecule as shown in SEQ ID NO: 4-9 is incorporated into a construct such that a promoter of the present invention is operably linked to a transcribable nucleic acid molecule that is a gene of agronomic interest. As used herein, the term "gene of agronomic interest" refers to a transcribable nucleic acid molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. No. 5,633,435 and U.S. Pat. No. 5,463,175), increased yield (U.S. Pat. No. 5,716,837), insect control (U.S. Pat. No. 6,063,597; U.S. Pat. No. 6,063,756; U.S. Pat. No. 6,093,695; U.S. Pat. No. 5,942,664; and U.S. Pat. No. 6,110,464), fungal disease resistance (U.S. Pat. No. 5,516,671; U.S. Pat. No. 5,773,696; U.S. Pat. No. 6,121,436; U.S. Pat. No. 6,316,407, and U.S. Pat. No. 6,506,962), virus resistance (U.S. Pat. No. 5,304,730 and U.S. Pat. No. 6,013,864), nematode resistance (U.S. Pat. No. 6,228,992), bacterial disease resistance (U.S. Pat. No. 5,516,671), starch production (U.S. Pat. No. 5,750,876 and U.S. Pat. No. 6,476,295), modified oils production (U.S. Pat. No. 6,444,876), high oil production (U.S. Pat. No. 5,608,149 and U.S. Pat. No. 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. No. 5,985,605 and U.S. Pat. No. 6,171,640), biopolymers (U.S. Pat. No. 5,958,745 and U.S. Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). The genetic elements, methods, and transgenes described in the patents listed above are hereby incorporated by reference.

Alternatively, a transcribable nucleic acid molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any nucleic acid molecule that encodes a protein or mRNA that expresses a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign nucleic acid molecule, such as a construct. The introduced nucleic acid molecule may be integrated into the genomic DNA of the recipient cell, tissue, organ, or organism such that the introduced nucleic acid molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign nucleic acid molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. No. 5,015,580; U.S. Pat. No. 5,550, 318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,824,877; U.S. Pat. No. 5,591,616; U.S. Pat. No. 5,981,840; and U.S. Pat. No. 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

ZM39486 Gene Identification

Expressed sequence tag (EST) library comparison was used to identify genes selectively expressed in corn endosperm and kernel tissues but not in any other tissues. EST library comparison was done using sequences from corn endosperm and kernel libraries vs. sequences from other reference libraries including leaf, root, stem, embryo, silks, seedling, shoot, anther, sheath, meristem, pollen, etc. EST sequences were identified as being present in the endosperm and kernel libraries but not in the reference libraries. Candidate EST sequences were then used for a more stringent blast analysis and electronic northern analysis to confirm that expression only appeared in endosperm libraries including a 5-8 days after pollination (DAP) endosperm library and whole kernel libraries.

RNA was then isolated from maize tissue for northern Blot confirmation of the expression pattern for the top candidate EST sequences. RNA was extracted from frozen maize tissues. For leaf, root, shoot and tassel, Trizol (Invitrogen catalog number 15596018) was used with the standard protocol provided by the manufacturer (Invtitrogen Corporation; Carlsbad, Calif.). For embryo and endosperm tissues, a modified Trizol method was used as follows: Frozen tissues were first ground in liquid nitrogen. Approximately 5 ml of lysis buffer (NaCl, 100 mM Tris-HCl (pH 8.8), 10 mM EDTA, and 1% sarkosyl with phenol/chloroform) was then added to 2 grams of ground tissue. The resultant mixture was incubated on ice for 5-10 minutes and then centrifuged at 4° C. for 15 minutes. The supernatant was transferred to a fresh tube and extracted with an equal volume of Trizol. For each 1 ml of Trizol reagent 0.2 ml of chloroform was added. The supernatant was transferred to a fresh tube after 15 minutes centrifugation at 4° C., and the RNA was precipitated using isopropanol.

20 µg of total RNA for each tissue was fractionated on formaldehyde-agarose gel and transferred to HybondN+ membrane (Amersham catalog number RPN203B) according to the manufacturer's instructions (Amersham Biosciences Corporation; Piscataway, N.J.). Membranes were prehybridized and hybridized in Rapid-hyb buffer (Amersham catalog number RPN1635) at 65° C. following manufacturer's guidelines (Amersham Biosciences Corporation; Piscataway, N.J.). $^{32}$P labeled DNA probe specific for each of the candidate EST sequences was added to the hybridization buffer. Northern Blot results confirmed the expression pattern observed in the library comparison analysis for the ZM39486 EST sequence.

Different vegetative and reproductive tissues were then collected and subjected to real-time RT-PCR (Taqman) analysis using primers specific to the ZM39486 cDNA. Tissues analyzed included nodal and radicle roots, stem, sheath, the top and basal portions of three different leaf blades, the spikelets, and the endosperm. Taqman analysis was conducted using an ABI Prism® 7700 Sequence Detection System (Product Number 7700-01-220/240) or an ABI Prism® 7900 Sequence Detection System (Product Number 4331406) and the standard protocols supplied by the manufacturer (Applied Biosystems; Foster City, Calif.). Quantitative RNA measurements are relative to a standardized control, and therefore unitless. Data are provided in Table 1 below.

TABLE 1

Analysis of Native ZM39486 RNA in Non-transgenic Corn Plants.

| Tissue | ZM39486 RNA Expression Level |
|---|---|
| Nodal Root | 15.9 +/− 1.6 |
| Radicle Root | 4.1 +/− 0.9 |
| Stem | 8.1 +/− 0.8 |

TABLE 1-continued

Analysis of Native ZM39486 RNA in Non-transgenic Corn Plants.

| Tissue | ZM39486 RNA Expression Level |
| --- | --- |
| Sheath | 4.0 +/− 0.1 |
| Leaf V6 Basal | 11.2 +/− 1.8 |
| Leaf V6 Top | 7.5 +/− 0.5 |
| Leaf V9 Basal | 1.5 +/− 0.4 |
| Leaf V9 Top | 8.6 +/− 0.4 |
| Leaf V11 Basal | 14.9 +/− 1.6 |
| Leaf V11 Top | 2.5 +/− 0.4 |
| Tassel/Spikelet | 4.7 +/− 1.3 |
| Endosperm (10 DAP) | 20,282.0 +/− 458 |

ZM39486 expression was found to be highly endosperm specific. Of all the tissues assayed, only the endosperm showed a high level of expression, whereas all other tissues had negligible levels of ZM39486 RNA.

Example 2

P-Zm.39486 Promoter Isolation and Cloning

The upstream promoter region for the ZM39486 gene was isolated and cloned from maize genomic DNA. The 5' upstream promoter fragment of ZM39486 was isolated using the Universal GenomeWalker™ Kit (BD Biosciences Clontech catalog number K1807-1) and the protocol provided by the manufacturer (BD Biosciences; San Jose, Calif.) with the following modifications: Leaf tissue from maize seedlings was harvested 10 days after planting. Genomic DNA was isolated from this tissue using a CsCl purification protocol according to Current Protocols in Molecular Biology (1994) Ausubel, F. M, Brent, R., Kingston, R. E., Moore, D. D., Seidman, J. G., Smith, J. A. and Struhl, K. (Eds.), Greene and Wiley-Intersceince, New York. Libraries for the GenomeWalker™ procedure were prepared according to manufacturer instructions (BD Biosciences; San Jose, Calif.). GenomeWalker™ libraries were then subjected to a primary round of PCR amplification with a first ZM39486 gene specific primer, 39486GSP1 (SEQ ID NO: 1), and the AP1 primer from the GenomeWalker™ kit that anneals the adaptor sequence. A diluted (1:50) aliquot of primary PCR reaction was used as the input DNA template for secondary nested PCR amplification, which used a second ZM39486 gene specific primer, 39486GSP2 (SEQ ID NO: 2), and the AP2 primer from the GenomeWalker™ kit. PCR conditions and components were modified as follows. The 50 μl primary PCR reaction included: 1 μl of GenomeWalker™ library, 25 pmol of 39486GSP1 (SEQ ID NO: 1), 25 pmol of AP1, 0.2 mM of dNTP mix, 1 μl of High fidelity Taq Polymerase (Roche catalog number 1 732 641), and 1×PCR buffer with 1.5 mM of $MgCl_2$ (Roche catalog number 1 732 641) (Roche Diagnostics Corporation Roche Applied Science; Indianapolis, Ind.). The PCR condition for the primary PCR reaction was: 3 minutes at 95° C., 7 cycles of 15 seconds at 95° C. and 3 minutes at 68° C., followed by 25 cycles of 15 seconds at 95° C. and 3 minutes at 65° C., ended with 3 minutes at 65° C. Components for the secondary nested PCR were the same as the primary PCR reaction except the DNA template was 1 μl of 1:50 dilution of primary PCR and the primers were 39486GSP2 (SEQ ID NO: 2) and AP2. The PCR condition for secondary PCR was: 2 minutes at 95° C., 5 cycles of 10 seconds at 95° C. and 3 minutes at 65° C., followed by 25 cycles of 10 seconds at 95° C. and 3 minutes at 60° C., ended with 3 minutes extension at 65° C.

The 1.6 kilobase (kb) fragment produced by the secondary PCR amplification was confirmed as the desired promoter fragment by 3' end-sequencing and comparison with an overlapping 5' 81 base pair (bp) region of the original ZM39486 EST sequence. This 1.6 kb fragment was then PCR amplified with primer BamHIBglII39486_1GSP2ATG (SEQ ID NO: 3) and primer AP2 again to produce a promoter fragment excluding any protein coding sequence. The new PCR product was cloned into the pCR2.1-TOPO vector (Invitrogen catalog number K4500-01) following the manufacturer's instruction (Invtitrogen Corporation; Carlsbad, Calif.). The full-length sequence of this promoter, referred to herein as P-Zm.39486 (SEQ ID NO: 4), was obtained and again compared to the overlapping 5' region of the original ZM39486 EST sequence to confirm that the correct promoter sequence was indeed cloned.

Example 3

P-Zm.39486 Characterization Using Qualitative GUS Staining Analysis

Qualitative histochemical analysis was done using stably transformed corn plants containing the gene for β-glucuronidase (GUS) operably linked to the P-Zm.39486 promoter. The P-Zm.39486 promoter was sub-cloned into a binary vector operably linked to the GUS gene (pMON17723), and then this construct was used to transform Zea mays LH172 through Agrobacterium-mediated transformation. Transgenic R0 events containing a single copy of the transgene were selected by real-time PCR analysis and advanced to homozygous R1 lines through self-pollination. The R1 and R2 homozygous lines were grown in the greenhouse under standard growth conditions, and multiple tissues were sampled at different developmental stages for GUS expression analysis. The sampled tissues included root, leaf (blade and sheath), stem, shoot apical meristem (SAM), inflorescence, anther, pollen, and kernel (endosperm and embryo).

Figure 1:
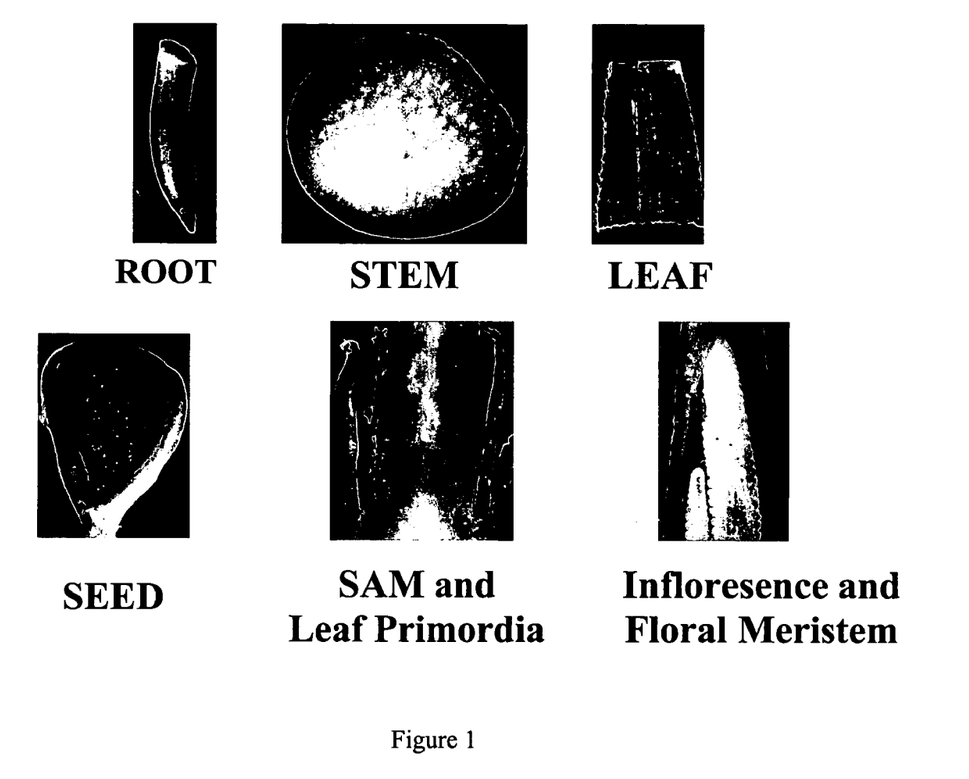
FIG. 1 represents GUS staining of tissues from a transgenic corn line transformed with the P-ZM.39486 promoter driving the GUS gene.
Figure 2:
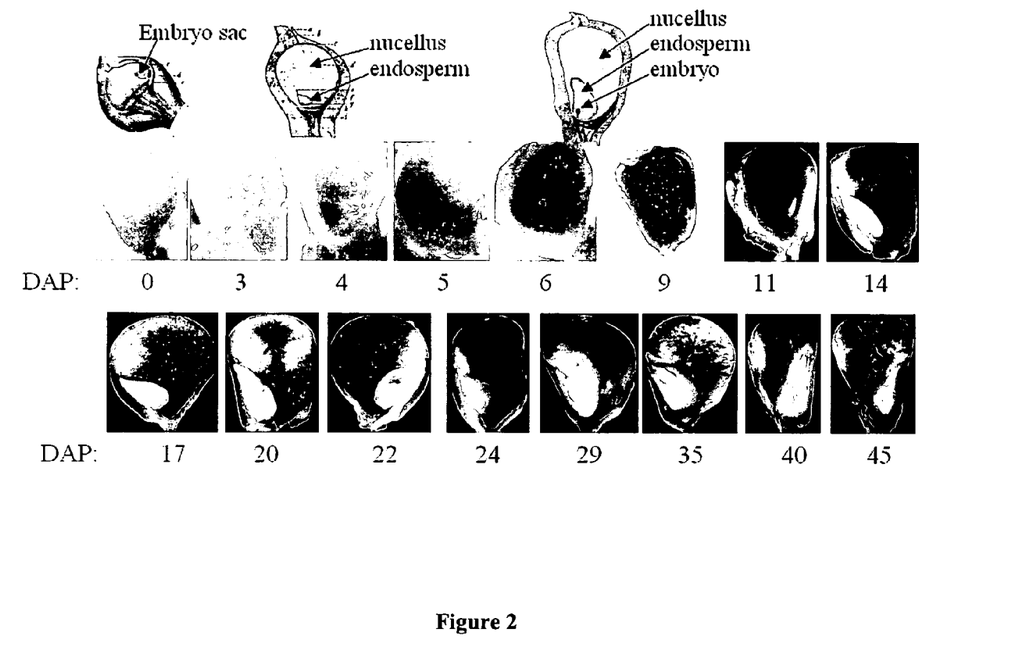
FIG. 2 represents GUS staining of kernels during early endosperm development from a transgenic corn line transformed with the P-ZM.39486 promoter driving the GUS gene.

Methods for measuring GUS activity are well known to those skilled in the art, see for instance Using the Gus Gene as a Reporter of Gene Expression (1992) edited by Sean R. Gallagher, Academic Press, Inc., San Diego. GUS staining was conducted using the β-Glucuronidase Reporter Gene Staining Kit (Sigma-Aldrich Company; St Louis, Mo.), following the procedure recommended by the manufacture, with minor modifications. Tissues samples were partially fixed for 10 minutes in 0.074% formaldehyde and 50 mM $NaPO_4$ pH7.0, and then incubated at 37° C. in staining solution using 5-Bromo-4-Chloro-3-Indolyl-β-D-Glucuronide (X-GlcA) as the substrate. For all tissues the incubation was at 37° C. overnight, with the exception of the kernels which were stained at 37° C. for 2 hours. After staining, tissues containing chlorophyll were destained in ethanol, and the treated tissues were examined and photographed under a dissecting microscope (FIGS. 1 and 2).

Multiple transgenic events were identified that showed predominantly kernel endosperm GUS staining. Table 2 shows the relative qualitative GUS expression level among different tissue types based on the intensity of GUS staining, with 10 as the strongest and 0 as no detectable staining.

TABLE 2

Qualitative GUS Expression driven by
P-Zm.39486 in Transgenic Corn.

| Tissue | GUS Staining time | Intensity |
|---|---|---|
| root | 12 hours | 1 |
| immature leaf | 12 hours | 0 |
| mature leaf blade | 12 hours | 0.5 |
| sheath | 12 hours | 0 |
| young stem | 12 hours | 1 |
| mature stem | 12 hours | 1.5 |
| male inflorescence | 12 hours | 0 |
| female inflorescence | 12 hours | 0 |
| anther | 12 hours | 0 |
| pollen | 12 hours | 0 |
| endosperm (12 DAP) | 2 hours | 10 |
| scutellum | 2 hours | 1 |
| scutellum-less embryo | 2 hours | 0 |

FIG. 1 also shows the GUS staining of multiple organs of a homozygous line including seed, root, stem, leaf, SAM and leaf primordia, and inflorescence and floral meristem. It is noteworthy that there was no staining in the shoot apical meristem or in the floral meristem, and that the weak staining in the root was not in the meristem area (tip), but rather in the differentiated area. These data indicate that P-Zm.39486 drives GUS gene expression predominantly in seed (kernel) tissue. Thus, the promoter could be used to drive coding sequences that may alter endosperm cell division or differentiation without having a negative effect on development of roots or shoots. The low level of expression observed in the stem and leaf was within the vascular tissues, perhaps suggesting a common origin of the transgene product.

To further investigate the developmental stage at which GUS expression was turned on by P-Zm.39486, kernels encompassing the entire seed developmental course, from the female reproductive tissue (placenta and ovule) just before fertilization at 0 DAP (days after pollination) to mature kernels at 50 DAP, were sampled for GUS staining. Whole kernels were cut from the center longitudinally, and were stained for GUS using the same procedure as described above. Data are provided in FIG. 2. Before fertilization took place (0 DAP), the female reproductive tissue had no detectable GUS expression. However, at 3 DAP (the earliest stage at which fertilized kernels were sampled, and the stage at which an endosperm cell mass of about 200-300 cells was detectable) GUS staining was seen in the developing endosperm, but not in the surrounding maternal nucellus tissues. From 4 DAP on, as the endosperm expanded rapidly as a result of active cell division, strong GUS staining accompanied and encompassed the entire endosperm mass. At 10-11 DAP, the embryo became visible, but was not stained, whereas the endosperm still showed strong GUS expression. At 14 DAP, the embryo was differentiated, and the scutellum appeared weakly stained, whereas the rest of the embryo was not stained at all. The strong endosperm GUS staining persisted into mature kernel stage, even when the cells were fully occupied by starch granules (e.g., 45 DAP). These data demonstrate that P-Zm.39486 directs strong kernel endosperm gene expression at a very early stage after fertilization (at least as early as 3 DAP). The promoter may also direct weak expression in the endosperm-contacting scutellum tissues.

Example 4

P-Zm.39486 Characterization Using Quantitative GUS Staining Analysis

Quantitative GUS analysis was done using stably transformed corn plants containing the gene for β-glucuronidase (GUS) operably linked to the P-Zm.39486 promoter. The P-Zm.39486 promoter was sub-cloned into a vector operably linked to the GUS gene (pMON17719) and then this construct was used to transform *Zea mays* H99 using microprojectile bombardment and the isolated cassette.

Transgenic events (R0) were screened for marker gene expression. Positive R0 events were then crossed with non-transgenic H99 plants to produce the heterozygous F1 generation. Tissue from various organs, developmental stages, and inducing conditions from these positive F1 events were then used for quantitative GUS analysis. The sampled tissues included imbibed seed, coleoptile, root, leaf, cob, anther, and kernel (endosperm and embryo).

Data for four lines (ZM_B6977, ZM_B7624, ZM_B9487, and ZM_B9489) are provided in Table 3 below. Table 3 provides quantitative GUS enzyme activity as pMole of MU/μg protein/h). Abbreviations used: DAG—Days After Germination; DAP—Days After Pollination; V3—three leaf stage; V7—Seven leaf stage; VT—Tasseling stage; nd—not determined. A measured value of <0.1 was activity less than the enzyme blank. A measured value of <20 was not considered to be significant as it was not above the measurable background activity. Cold inducement was measured as plants exposed to 15° C. for 24 hours. Desiccation inducement was measured as live wilting of plants induced by withholding irrigation until 50% loss of moisture.

TABLE 3

Quantitative GUS Expression Driven by P-Zm.39486 in Transgenic Corn.

| Stage | Organ | Inducer | ZM_B6977 | ZM_B7624 | ZM_B9487 | ZM_B9489 |
|---|---|---|---|---|---|---|
| Imbibed seed | Embryo | None | <0.1 | <0.1 | 32.34 | <0.1 |
| Imbibed seed | Endosperm | None | <0.1 | 29.46 | 65.33 | <0.1 |
| 3DAG | Root | None | 36 | <0.1 | <0.1 | <0.1 |
| 3DAG | Coleoptile | None | <0.1 | 93.8 | 36 | 74 |
| V3 | Root | None | <0.1 | <0.1 | nd | <0.1 |
| V3 | Leaf | None | <0.1 | <0.1 | nd | 19.6 |
| V3 | Root | Cold | <0.1 | 1.8 | nd | 3.5 |
| V3 | Leaf | None | <0.1 | <0.1 | nd | <0.1 |
| V3 | Root | Desiccation | <0.1 | <0.1 | nd | 59.6 |
| V3 | Leaf | None | <0.1 | <0.1 | nd | <0.1 |
| V7 | Root | None | 3.25 | 4 | nd | 11 |
| V7 | Leaf - young | None | 79 | 8.6 | nd | 3.5 |
| V7 | Leaf - mature | None | 15 | 10.85 | nd | 13 |
| VT | Root | None | <0.1 | 7.3 | nd | <0.1 |

TABLE 3-continued

Quantitative GUS Expression Driven by P-Zm.39486 in Transgenic Corn.

| Stage | Organ | Inducer | ZM_B6977 | ZM_B7624 | ZM_B9487 | ZM_B9489 |
|---|---|---|---|---|---|---|
| VT | Leaf - mature | None | <0.1 | <0.1 | nd | 5.1 |
| VT | Leaf - Senescence | None | 25 | <0.1 | nd | 6 |
| VT | Cob | None | 11 | 10 | nd | 2.2 |
| VT | Anther | None | 6 | 18.7 | nd | 10 |
| 7 DAP | Kernel | None | 135 | 201 | 30.2 | 416.9 |
| 14 DAP | Embryo | None | 61.6 | 22.86 | 27.1 | <20 |
| 14 DAP | Endosperm | None | 128 | 179 | 205 | 40 |
| 21 DAP | Embryo | None | 22.5 | <20 | <20 | <0.1 |
| 21 DAP | Endosperm | None | 40.5 | <20 | <0.1 | <0.1 |
| 35 DAP | Embryo | None | <0.1 | <20 | <0.1 | <0.1 |
| 35 DAP | Endosperm | None | 75.5 | <20 | <0.1 | <0.1 |

Quantitative GUS analysis showed strong GUS enzyme activity in the whole kernel 7 DAP (embryo and endosperm were not separated) and in the endosperm 14 DAP, but not in the embryo 14 DAP. This pattern is consistent with earlier results (Table 2 and FIGS. 1 and 2). Because this quantitative activity assay required manual dissection of endosperm and embryo tissues from the kernel, a small amount of contaminating endosperm tissue could cause the low level of GUS activity measured in some embryo samples.

Weak GUS activity could also be detected in other tissues tested across different developmental stages. This pattern was not consistently found in the four lines, though, so it may be due to the normal variation found in transgenic plants. Variation among transgenic events has been well documented. While it has been generally attributed to "positional effect", mechanistically, this could be caused by the state of the chromatin, the influence of nearby regulatory elements, copy number of the transgene, and arrangement of multiple transgenes within the integration site.

Example 5

P-Zm.39486 Promoter Characterization Using Quantitative RNA Analysis

Since GUS is known to be a very stable protein, GUS staining alone is not an optimal method for determining precisely when the promoter driving the GUS expression is turned off. Therefore, to determine when P-Zm-39486 is turned off during kernel endosperm development, RNA levels of both the native downstream gene (ZM39486) in non-transgenic plants and the GUS transgene driven by P-Zm-39486 in transgenic plants was analyzed. Real-time RT-PCR (Taqman) analysis was conducted using an ABI Prism® 7700 Sequence Detection System (Product Number 7700-01-220/240) or an ABI Prism® 7900 Sequence Detection System Product Number 4331406) and the standard protocols supplied by the manufacturer (Applied Biosystems; Foster City, Calif.). Samples were analyzed from whole kernels from 0 DAP to 45 DAP using gene specific primers. Data is provided in Table 4 below. Quantitative RNA measurements are relative to a standardized control, and therefore unitless.

TABLE 4

Analysis of RNA levels during Kernel Development in Corn Plants.

| DAP | Kernel GUS RNA (transgenic) | Kernel ZM39486 RNA (non-transgenic) |
|---|---|---|
| 3 | 1158 +/− 37 | 921 +/− 255 |
| 5 | 1674 +/− 84 | 573 +/− 65 |
| 7 | 1135 +/− 141 | 2624 +/− 92 |
| 9 | 2054 +/− 140 | 4389 +/− 219 |
| 11 | 1761 +/− 129 | 5970 +/− 409 |
| 14 | 1198 +/− 51 | 21532 +/− 644 |
| 16 | 793 +/− 57 | 19305 +/− 631 |
| 20 | 613 +/− 52 | 601 +/− 36 |
| 24 | 517 +/− 68 | 6 +/− 2 |
| 29 | 717 +/− 81 | 630 +/− 51 |
| 35 | 495 +/− 72 | 5 +/− 2 |
| 40 | 274 +/− 17 | 3 +/− 1 |
| 45 | 390 +/− 58 | 440 +/− 28 |

Data presented in Table 4 above demonstrate that for both the GUS transgene and the native ZM39486 gene the expression of RNA directed by P-Zm.39486 was turned on 3 DAP, thus confirming previous GUS staining results (FIG. 2). For the GUS transgene, the total RNA accumulation in kernels reached its highest level at about 9 DAP, and then decreased slowly after 11 DAP. Because GUS RNA is relatively stable, the observed GUS RNA accumulation at later stages of kernel development is likely to reflect the carry over RNA rather than in situ gene expression. For the native AM39486 gene, the total RNA accumulation in kernels reached its highest level at about 14-16 DAP, and then decreased significantly after 16 DAP. At 20 DAP, the ZM39486 RNA level dropped dramatically to background level, suggesting that the expression of ZM39486, driven by its native promoter was turned off at 20 DAP.

Staining of kernel slices for GUS activity has previously demonstrated that gene expression directed by P-Zm.39486 was restricted in kernels to the developing endosperm and to the scutellum (Table 2, FIGS. 1 and 2). Furthermore, the contribution to GUS staining in the kernel by the scutellum was small. Therefore, since the endosperm cells comprise only a small percentage of the kernel at days 3-7 of kernel development (FIG. 2), the quantitative assay for GUS activity in whole kernels at early stages of kernel development (Table 3) provides an underestimate of the activity of the promoter in endosperm cells during early kernel development. To compensate for this, the RNA levels were normalized by adding back the dilution factor due to the maternal nucellus tissues in order to obtain a more quantitative endosperm expression level assessment. Data are provided in Table 5 below.

TABLE 5

Analysis of Normalized RNA levels during Kernel Development in Corn Plants.

| DAP | Kernel GUS RNA (transgenic) | Kernel ZM39486 RNA (non-transgenic) |
|---|---|---|
| 3 | 53489 +/− 256 | 42535 +/− 1736 |
| 5 | 44296 +/− 434 | 15170 +/− 337 |
| 7 | 4683 +/− 374 | 10828 +/− 187 |
| 9 | 4109 +/− 199 | 8779 +/− 310 |
| 11 | 2642 +/− 158 | 8955 +/− 5011 |
| 14 | 1198 +/− 51 | 21532 +/− 644 |
| 16 | 793 +/− 57 | 19305 +/− 631 |
| 20 | 613 +/− 52 | 601 +/− 36 |
| 24 | 517 +/− 68 | 6 +/− 2 |
| 29 | 717 +/− 81 | 630 +/− 51 |
| 35 | 495 +/− 72 | 5 +/− 2 |
| 40 | 274 +/− 17 | 3 +/− 1 |
| 45 | 390 +/− 58 | 440 +/− 28 |

The normalized analysis demonstrated that for both the GUS transgene and the native ZM39486 gene the expression of RNA directed by P-Zm.39486 was strongest at 3 DAP in developing endosperm. The GUS RNA levels decreased dramatically after 5 DAP. At 20 DAP, the total GUS RNA accumulation in expressing tissues had decreased by approximately 90 fold. Native ZM39486 RNA accumulation was turned off at 20 DAP.

Native ZM39486 expression driven by the native P-Zm.39486 promoter was found to be highly endosperm specific: of all the tissues assayed, only the endosperm showed a high level of expression, whereas all other tissues had no detectable ZM39486 RNA (Table 1). This expression pattern for P-Zm.39486 was confirmed driving a transgene in transgenic plants using GUS staining (Tables 2 and 3, FIG. 1). Although the GUS staining patterns driven by P-Zm.39486 in transgenic plants do show some minor leakiness in tissues other than the kernel endosperm (Tables 2 and 3, FIG. 1), the strict kernel endosperm expression pattern revealed by the native ZM39486 gene expression (Tables 1, 4, and 5) is likely a more accurate reflection of the authentic activity of this promoter. Our data also suggest that the P-Zm.39486 promoter is highly active in endosperm cells as early as 3 days after pollination, and may be active as soon as fertilized endosperm cells begin to divide (Tables 4 and 5, FIG. 2). The promoter then shuts off by 20 days after pollination (Tables 4 and 5).

Example 6

P-Zm.39486 Truncation and Rice Homolog Identification

The full length P-Zm.39486 sequence was analyzed in order to create desirable truncation variants. A region from approximately 769 to 1021 bp (relative to the full-length version) was selected for deletion to produce the first truncation variant (SEQ ID NO: 5). A second truncation variant (SEQ ID NO: 6) was produced by trimming the full-length promoter to include only 1022 to 1563 bp (relative to the full-length version).

The homologous rice promoter for P-Zm.39486 was obtained by first identifying the homologous gene sequence in rice. The DNA sequence of the ZM39486 EST was first translated into a protein sequence which was then used as the query sequence to search a dataset containing predicted proteins produced from rice genomic DNA. Searches were done using standard BLAST analysis (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs" *Nucleic Acids Research* 25:3389-3402). The search identified a region in a gDNA BAC clone, B1108H10, of rice chromosome 1 homologous to the ZM39486 sequence. The start codon for the rice gene was then identified and the upstream promoter sequence was determined and designated as P-Os.39486 (SEQ ID NO: 7). The full length P-Os.39486 sequence was analyzed in order to create desirable truncation variants. A region from approximately 1099 to 1222 bp (relative to the full-length version) was selected for deletion to produce the first truncation variant (SEQ ID NO: 8). A second truncation variant (SEQ ID NO: 9) was produced by trimming the full-length promoter to include only 1223 to 1801 bp (relative to the full-length version).

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. An isolated nucleic acid molecule selected from the group consisting of
   a) a nucleic acid molecule comprising at least 95 contiguous bases of SEQ ID NO:4, wherein the nucleic acid has promoter activity that drives expression predominantly in seed tissue; and
   b) a nucleic acid molecule comprising the nucleic acid sequence of SEQ ID NO:4.

2. An isolated nucleic acid molecule comprising the nucleic acid sequence of SEQ ID NO: 4.

3. The isolated nucleic acid molecule according to claim 1, wherein said isolated nucleic acid molecule comprises at least 125 contiguous bases of SEQ ID NO: 4.

4. The isolated nucleic acid molecule according to claim 1, wherein said isolated nucleic acid molecule comprises at least 250 contiguous bases of SEQ ID NO: 4.

5. The isolated nucleic acid molecule according to claim 1, wherein said isolated nucleic acid molecule comprises at least 400 contiguous bases of SEQ ID NO: 4.

6. A construct comprising an isolated nucleic acid molecule comprising at least 95 contiguous bases of SEQ ID NO:4, wherein the nucleic acid molecule has promoter activity that drives expression predominantly in seed tissue and wherein said nucleic acid molecule is operably linked to a transcribable nucleic acid molecule operably linked to a 3' transcription termination nucleic acid molecule.

7. The construct of claim 6, wherein said transcribable nucleic acid molecule is a gene of agronomic interest.

8. The construct of claim 6, wherein said transcribable nucleic acid molecule is a marker gene.

9. A construct comprising the isolated nucleic acid molecule of claim 1, wherein said nucleic acid molecule is operably linked to a transcribable nucleic acid molecule operably linked to a 3' transcription termination nucleic acid molecule.

10. The construct of claim 9, wherein said transcribable nucleic acid molecule is a gene of agronomic interest.

11. The construct of claim 9, wherein said transcribable nucleic acid molecule is a marker gene.

12. A transgenic plant stably transformed with a construct comprising an isolated nucleic acid molecule comprising at least 95 contiguous bases of SEQ ID NO:4, wherein the nucleic acid molecule has promoter activity that drives expression predominantly in seed tissue and wherein said nucleic acid molecule is operably linked to a transcribable nucleic acid molecule operably lined to a 3' transcription termination nucleic acid molecule.

13. The transgenic plant of claim 12, wherein said plant is a monocotyledonous selected from the group consisting of wheat, maize, rye, rice, oat, barley, turfgrass, sorghum, millet and sugarcane.

14. The transgenic plant of claim 12, wherein said plant is a dicotyledonous plant selected from the group consisting of tobacco, tomato, potato, soybean, cotton, canola, sunflower and alfalfa.

15. A seed of said transgenic plant of claim 12, wherein the seed comprises said construct.

16. A transgenic plant stably transformed with a construct comprising an isolated nucleic acid molecule comprising the nucleic acid sequence of claim 1 wherein said nucleic acid molecule is operably linked to a transcribable nucleic acid molecule operably lined to a 3' transcription termination nucleic acid molecule.

17. The transgenic plant of claim 16, wherein said plant is a monocotyledonous selected from the group consisting of wheat, maize, rye, rice, oat, barley, turfgrass, sorghum, millet and sugarcane.

18. The transgenic plant of claim 16, wherein said plant is a dicotyledonous plant selected from the group consisting of tobacco, tomato, potato, soybean, cotton, canola, sunflower and alfalfa.

19. A seed of said transgenic plant of claim 16, wherein the seed comprises said construct.

20. The transgenic plant of claim 16, wherein the isolated nucleic acid molecule comprises at least 125 contiguous bases of SEQ ID NO: 4.

21. The transgenic plant of claim 16, wherein the isolated nucleic acid molecule comprises at least 250 contiguous bases of SEQ ID NO: 4.

22. The transgenic plant of claim 16, wherein the isolated nucleic acid molecule comprises at least 400 contiguous bases of SEQ ID NO: 4.

* * * * *

UNITED STATES PATENT AND TRADEMARK OFFICE
CERTIFICATE OF CORRECTION

| | | |
|---|---|---|
| PATENT NO. | : 7,518,035 B2 | Page 1 of 1 |
| APPLICATION NO. | : 11/086904 | |
| DATED | : April 14, 2009 | |
| INVENTOR(S) | : Cheikh et al. | |

It is certified that error appears in the above-identified patent and that said Letters Patent is hereby corrected as shown below:

In Claim 1, column 27, line 23, insert --molecule-- after the word acid.

In Claim 12, column 28, line 22, delete "lined" and insert --linked--.

In Claim 16, column 28, line 38, delete "lined" and insert --linked--.

Signed and Sealed this

Twenty-sixth Day of May, 2009

JOHN DOLL
*Acting Director of the United States Patent and Trademark Office*